United States Patent [19]

Bachmann et al.

[11] 4,223,443
[45] Sep. 23, 1980

[54] STRAIN PICK-UP FOR TESTING OF MATERIALS

[75] Inventors: Volker Bachmann, St. Augustin; Horst Nowack, Vollmarstein; Karl-Heinz Trautmann, St. Augustin, all of Fed. Rep. of Germany

[73] Assignee: Deutsche Forschungs- und Versuchsanstalt fur Luft- und Raumfahrt e.V., Cologne, Fed. Rep. of Germany

[21] Appl. No.: 28,537

[22] Filed: Apr. 9, 1979

[30] Foreign Application Priority Data

Apr. 15, 1978 [DE] Fed. Rep. of Germany ....... 2816444

[51] Int. Cl.$^3$ .............................................. G01B 5/00
[52] U.S. Cl. ................................................ 33/148 D
[58] Field of Search ................ 73/760, 774, 786, 787, 73/795, 826, 831, 833, 855; 33/148 D, 147 D, DIG. 13

[56] References Cited

U.S. PATENT DOCUMENTS

| | | | |
|---|---|---|---|
| 2,316,975 | 4/1943 | Ruge | 33/148 H |
| 2,611,966 | 9/1952 | Rebman | 73/750 |
| 2,681,566 | 6/1954 | Ruge | 33/DIG. 13 |
| 3,789,508 | 2/1974 | Meline | 33/148 D |
| 3,853,000 | 12/1974 | Barnett et al. | 33/DIG. 13 |

FOREIGN PATENT DOCUMENTS 728345 12/1966 Italy .......................................... 73/760

*Primary Examiner*—Harry N. Haroian
*Attorney, Agent, or Firm*—Spensley, Horn, Jubas & Lubitz

[57] ABSTRACT

A strain gauge pick-up for the measurement of a test piece. This pick-up includes two tapping points mounted on a pair of rigid elbow members. The elbow members are spaced a predetermined distance apart, and their spacing varies as the tapping points are applied to the test piece. The elbow members are attached to the deflection plate which flexes as the spacing between the elbow members changes. A wire strain gauge is positioned on the deflection plate and senses the flexing motion. Several pick-ups can be integrated so that their tapping points are substantially colinear.

6 Claims, 5 Drawing Figures

4,223,443

STRAIN PICK-UP FOR TESTING OF MATERIALS

BACKGROUND OF THE INVENTION

1. Field of the Invention

The invention relates to a strain pick-up for testing of materials, wherein two tapping points which are applied to a test piece are mounted on rigid elbow members, the spacing of which can be changed within limits.

2. Description of the Prior Art

There are known strain pick-ups in which the two tapping points are attached to rigid elbow members which form the ends of a casing and are displaceable relative to one another. In order to convert the magnitude of displacement into electrical analog data, there is provided induction equipment in which a magnetic core is located symmetrically between two coils. The magnetic core, which is coupled to one of the two displaceable ends, is displaced relative to the coils upon a change in the distance between the tapping points, whereby the symmetry of a measuring bridge is disturbed. Such strain pick-ups are expensive and bulky, and are relatively heavy in weight because of the coils and cores. Several such strain pick-ups may be employed at the same time, but must always be a definite minimum distance apart. Measurements of strain distributions and strain gradients within the limits of stress concentrations are very difficult with the known instruments.

SUMMARY OF THE INVENTION

An object of the present invention is to provide a strain pick-up of the type initially mentioned, which is simple in construction and inexpensive to manufacture, yet having good linearity and enabling relatively high accuracies of measurement.

In fulfillment of this purpose, provision is made according to the invention for the two elbow members to be connected by a deflecting spring or plate upon which is mounted at least one wire strain gauge.

The investigation of strain by wire strain gauges is considerably cheaper and simpler than by inductive measuring devices. The elbow members are moved apart linearly upon extension of the test piece. This linear movement of the elbow members causes a deflection of the deflecting spring. This deflection is measured and electrically evaluated with the wire strain gauges of which one is preferably arranged on each side of the deflecting spring. This results in excellent linearity between strain path and measuring voltage.

The tapping points are mounted on the free limbs of the two elbow members and the free limbs are aligned with one another.

At the side of the deflecting spring remote from the tapping points, there may be fixed two additional elbow members the free ends of which are separated from one another by an air gap. Moreover, each of the first elbow members is connected with one of the additional elbow members, so that, upon a movement of the two tapping points relative to one another, the additional elbow members are also moved. If the tapping points are moved away from one another, then the free limbs of the additional elbow members are moved towards one another until they finally come together and thus limit the measuring range and prevent overloading of the deflecting spring.

In order to be able to determine stress distributions or stress gradients in regions of localized stress concentration, it is occasionally necessary to locate pairs of tapping points very close together, or even to nest one pair within another. Such an arrangement is made possible because of the extremely simple mechanical construction of the strain pick-up according to the present invention. For this purpose, the elbow members together with the deflecting spring, considered in side elevation, almost entirely enclose an open space into which a similar strain pick-up of smaller dimensions may be inserted in such a way that the tapping points of the two strain pick-ups are at least substantially in alignment.

It is thus a prerequisite for this that similar strain pick-ups are available in different sizes, so that in each case the smaller strain pick-up fits into the space enclosed by the larger strain pick-up. The tapping points of all pick-ups fitted into one another have different lengths and are so dimensioned that the ends of all points are at least substantially in alignment.

If only one strain pick-up is to be used for very precise measurements, the ends of the space enclosed by the elbow members and the deflecting spring may be closed off by end plates of which each is rigidly connected with only one of the elbow members. The end plates hold air currents off from the deflecting spring, and prevent disturbing effects from other environmental influences on the measurement result. The end plates are each connected with only one of the elbow members, in order to preserve the relative mobility of the other elbow member.

BRIEF DESCRIPTION OF THE DRAWINGS

Embodiments of the invention will be explained in more detail in the following with reference to the figures.

DESCRIPTION OF THE PREFERRED EMBODIMENTS

Figure 1:
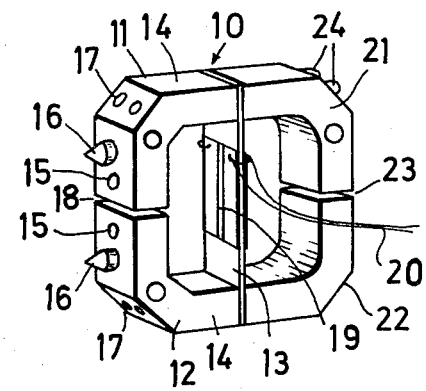
FIG. 1 is a perspective view of a first embodiment of the strain pick-up without side plates.

The strain pick-up 10 in FIG. 1 consists of two similar elbow members 11, 12 which are connected together by the deflecting spring 13. Each of the elbow members 11, 12 has one limb 14, extending at right angles to and abutting the deflecting spring 13. Each elbow member 11 and 12 includes a second limb 15, upon which there is a tapping point 16, which is interchangeably mounted. The tapping points 15 are directed away from the deflecting spring 13. The two limbs 14 and 15 each pass through a transition piece 17 which extends at 45° over into each of the limbs.

The free limbs 15, upon which the tapping points 16 are located, are separated from one another by a gap 18. Wire strain gauges 19 are mounted on both surfaces of the blade-shaped deflecting spring 13. Electric cables 20 lead from the gauges 19 to a test amplifier (not shown).

In the embodiment according to FIG. 1, there are provided two additional elbow members 21, 22 which have the same shape and dimensions as the elbow members 11, 12. These elbow members 21, 22 are arranged symmetrically with respect to the elbow members 11, 12 on the opposite side of the deflecting spring 13, and the free limbs thereof form a gap 23 which is reduced when the two tapping points 16 are moved away from one another. In this way the gap 23 limits the strain range, and prevents overloading of the spring 13 or of the wire strain gauges 19.

As FIG. 1 shows, the two elbow members 11 and 21 are connected together by screws 24, which extend through appropriate holes in the deflecting spring, and extend longitudinally through the limbs 14. The screws 24 secure one end of the deflecting spring 13 between the end surfaces of the limbs 14 of the two elbow members 11 and 21. In the same way, screws (not shown) extend through the lower limbs 14 of the two elbow members 12 and 22, in order to secure the other end of the deflecting spring 13.

When in use, the deformation of the deflecting spring 13 results from increase of the distance between the tapping points 16. When this occurs, the air-gap 18 is increased, while air-gap 23 is reduced, and the deflecting spring 13 is exposed to an almost pure bending strain. The bending of the deflecting spring 13 is detected by means of the wire strain gauge 19.

Figure 2:
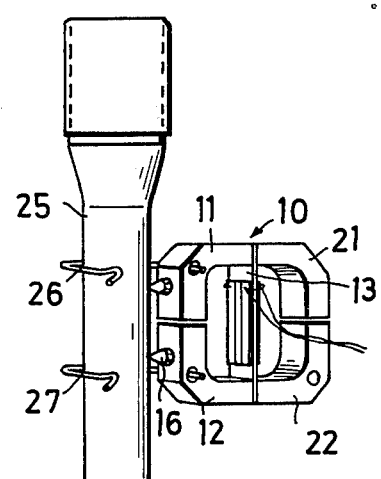
FIG. 2 shows the use of the strain pick-up according to FIG. 1 on a test piece, and its attachment to the test piece by a holder.

FIG. 2 shows the use of the strain pick-up 10 on a rod-shaped test piece 25. The two tapping points 16 are applied to the test piece 25 and are kept pressed firmly against the surface of the test piece by a pair of clips 26, 27. The clips 26, 27 surround the test piece, and are attached to holes in the elbow members 11 and 12. The clips 26 and 27 are flexible, and force the tapping points 16 against the test piece such that the tapping points 16 do not shift during the entire test on the test piece 25.

Figure 3:
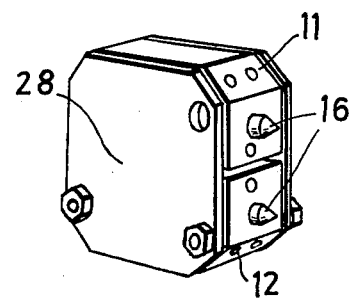
FIG. 3 shows the strain pick-up according to FIG. 1 with side plates.

FIG. 3 shows the strain pick-up according to FIG. 1 with additional face plates 28, which close off the sides of the space enclosed by the elbow members 11, 12 and 21 and 22 so that the deflecting spring 13 is protected from air currents and other external influences. The plates 28 are secured only to the elbow member 12, or to the additional elbow member 22 connected thereto, while the interconnected elbow members 11 and 21 can move relative to the face plates 28.

As will be clearly seen from the drawings, all four elbow members 11, 12, 21 and 22 are identical to one another, and are formed with similar limbs, so that as a whole they enclose roughly one square and the strain pick-up has approximately square overall dimensions.

Figure 4:
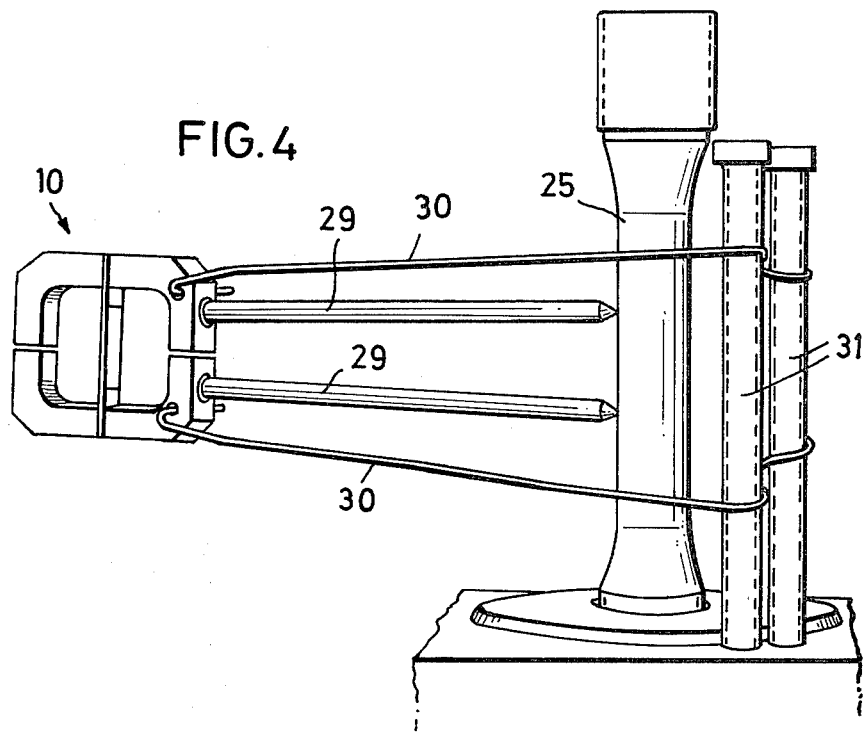
FIG. 4 shows the strain pick-up according to FIG. 1 with special tapping points for high temperature measurements, and a suitable specific embodiment of the holder.

As FIG. 4, shows, the tapping points are interchangeable. The tapping points 16 in this case are replaced by quartz arms 29, which are ground at their free ends to form contact blades or points. Attachment of the strain pick-up 10 to the test piece 25 is effected by suitable holders 30 or rubber struts, which engage according to FIG. 4 separate holding means 31, which is fixed relative to the test piece 25.

It is possible to manufacture the strain pick-up with small dimensions. In this way, on the one hand, intense localized strains may be determined, and, on the other hand, the pick-up may be used even in severely restricted spaces. The deflecting spring 13 is interchangeable, thus enabling the adaptation of the strain pick-up to any given test situation (sensitivity, etc.). Upon damage to the deflecting spring 13, it may be simply and rapidly replaced. The air-gaps 18 and 23 have an opening of about 0.5 to 1 mm.

Figure 5:
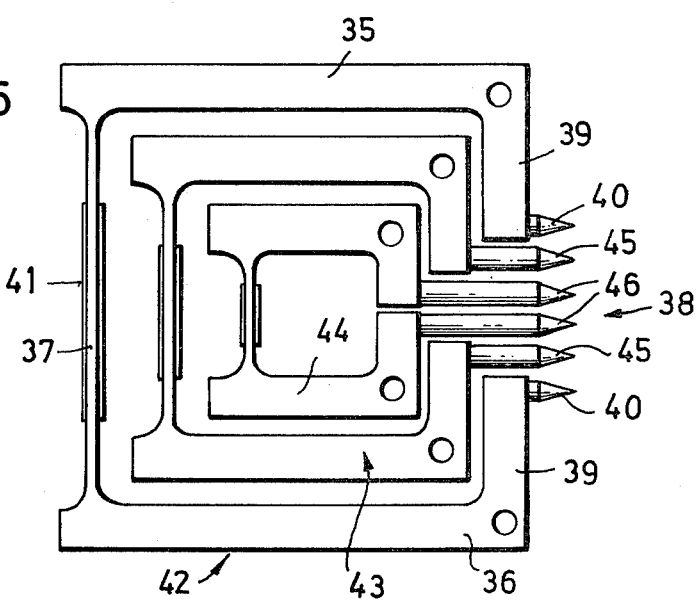
FIG. 5 shows a second embodiment using strain pick-ups in three different sizes in a strain pick-up system for determining strain distributions.

FIG. 5 shows a strain pick-up system having pick-ups of three different sizes 42, 43 and 44 fitted into one another.

Two elbow members 35 and 36 are connected together by a deflecting spring 37 which may be made integrally with the elbow members 35 and 36. The elbow members 35, 36 together with the deflecting spring 37 almost entirely enclose an approximately square space that includes a gap 38 between free ends 39 of the elbow members 35 and 36. The respective tapping points 40 are located on opposite sides of the gap 38.

If, as a result of elongation of the test piece (not shown), the tapping points 40 move away from one another, the deflecting spring 37 is bent, and the bending is ascertained by a wire strain gauge 41.

In the interior of the space enclosed by the largest strain pick-up 42 is located a second and similar strain pick-up 43, and in turn within the latter there is located a third similar strain pick-up 44. Tapping points 45 of the middle strain pick-up 43 project through the gap 38, and between them are tapping points 46 of the smallest strain pick-up 44.

The tapping points 40, 45 and 46 of all three strain pick-ups lie on a common straight line. This means that the tapping points 46 must be longer than the tapping points 45, and the latter in turn must be longer than the tapping points 40. This insertion within one another of the three strain pick-ups is effected with a degree of play allowing each of the strain pick-ups to deform freely, without interference from the other strain pick-ups. The strain pick-ups thus operate independently of one another. Depending on the testing requirements, they may be used in different numbers. With the help of this strain pick-up system, strain distributions and strain gradients may be determined within the limits of strain concentrations, on flat or curved test pieces. For example, the strain distribution in sectional test pieces may be measured to within the limits of significant plastic deformation. The attachment of the strain pick-ups is effected as in the first embodiment with the help of struts or ties.

Although particular embodiment of the invention have been described and illustrated herein, it is recognized that modifications and variations may readily occur to those skilled in the art and consequently it is intended that the claims be interpreted to cover such modifications and equivalents.

We claim:

1. A strain pick-up for testing of materials, comprising:
   a pair of tapping points applicable against a test piece;
   a pair of rigid elbow members each supporting one of said tapping points, the distance between said tapping points and hence between said elbow members changing within limits upon deformation of said test piece;
   a deflection plate secured to said elbow members remote from said tapping points;
   at least one wire strain gauge mounted on said deflection plate; and
   two additional elbow members fixed to the side of said deflection plate remote from the tapping points, the free ends of said additional elbow members being separated from one another by an air gap.

2. A strain pick-up according to claim 1 further including a pair of face plates, each secured to one of said elbow members, for covering a space enclosed by the elbow members and deflection plate.

3. The strain pick-up of claim 2 wherein the elbow members and deflection plate substantially enclose an open space in which at least one other like strain pick-up, having smaller dimensions is situated, the tapping points of all of said strain pick-ups being substantially aligned, said face plates also being secured to one of the elbow members of each other like strain pick-up.

4. A strain pick-up according to claim 1 wherein the tapping points are interchangeable.

5. A strain pick-up according to claim 1 further including a clip, attached to each of said elbow members which support the tapping points, for securing the pick-up to a holding device or test piece.

6. A system comprising:
- a plurality of strain pick-ups of sequentially increasing size, each pick-up comprising:
- a pair of tapping points applicable against a test piece;
- a pair of rigid elbow members, each supporting one of said tapping points, the distance between said tapping points and hence between elbow members changing within limits upon deformation of said test piece;
- a deflection plate secured to said elbow members remote from said tapping points;
- at least one wire strain gauge mounted on said deflection plate;
- the elbow members and deflection plate of each pick-up substantially enclosing an open space, smaller ones of said pick-ups being nested within the open spaces of the larger pick-ups, there being a gap between the ends of the elbow members of each pick-up;
- the tapping points of progressively smaller pick-ups being progressively longer, said longer tapping points extending through the gaps of the larger pick-ups, the terminal ends of all pick-ups being substantially aligned; and
- at least one face plate secured to one of said elbow members of each pick-up, for covering a space enclosed by the elbow members and deflection plates.

* * * * *